United States Patent
Matsui et al.

(10) Patent No.: US 8,058,473 B2
(45) Date of Patent: Nov. 15, 2011

(54) METHOD FOR PRODUCING ALPHA, BETA-UNSATURATED CALBOXYLIC ACID

(75) Inventors: Toshiki Matsui, Hiroshima (JP); Yoshiyuki Himeno, Hiroshima (JP); Kazunori Matake, Hiroshima (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 63 days.

(21) Appl. No.: 12/521,670

(22) PCT Filed: Dec. 26, 2007

(86) PCT No.: PCT/JP2007/074886
§ 371 (c)(1), (2), (4) Date: Jun. 29, 2009

(87) PCT Pub. No.: WO2008/081793
PCT Pub. Date: Jul. 10, 2008

(65) Prior Publication Data
US 2010/0137638 A1    Jun. 3, 2010

(30) Foreign Application Priority Data
Dec. 28, 2006  (JP) ................................. 2006-355863

(51) Int. Cl.
*C07C 51/16*    (2006.01)
(52) U.S. Cl. ....................................... 562/546; 562/533
(58) Field of Classification Search ................. 562/546, 562/533
See application file for complete search history.

(56) References Cited

U.S. PATENT DOCUMENTS

| | | | | |
|---|---|---|---|---|
| 3,624,147 A | * | 11/1971 | David et al. ................... | 562/546 |
| 3,969,274 A | * | 7/1976 | Frampton ..................... | 502/213 |
| 4,404,397 A | * | 9/1983 | Daniel .......................... | 562/546 |
| 2002/0151747 A1 | * | 10/2002 | Unruh et al. .................. | 562/546 |
| 2007/0173662 A1 | | 7/2007 | Fujimori et al. | |
| 2007/0238903 A1 | | 10/2007 | Ninomiya et al. | |

FOREIGN PATENT DOCUMENTS

| WO | 2005 075072 | 8/2005 |
|---|---|---|
| WO | 2005 118134 | 12/2005 |

OTHER PUBLICATIONS

Hawley Gessner, the Condensed Chemical Dictionary ,1975,Van Nostrand Reinhold Co., 8th ed.,p. 783.*

* cited by examiner

*Primary Examiner* — Taylor Victor Oh
(74) *Attorney, Agent, or Firm* — Oblon, Spivak, McClelland, Maier & Neustadt, L.L.P.

(57) ABSTRACT

Disclosed is a method for producing an α, β-unsaturated carboxylic acid from an olefin or an α, β-unsaturated aldehyde, while suppressing dissolution of a silica carrier, which is a carrier for a silica-supported noble metal-containing catalyst, in a water-containing solvent. Specifically disclosed is a method for producing an α, β-unsaturated carboxylic acid through oxidation of an olefin or an α, β-unsaturated aldehyde in a water-containing solvent in the presence of a silica-supported noble metal-containing catalyst in a reactor, in which at least one of silicic acid and ions thereof is supplied into the reactor.

19 Claims, No Drawings

METHOD FOR PRODUCING ALPHA, BETA-UNSATURATED CALBOXYLIC ACID

TECHNICAL FIELD

The present invention relates to a method for producing an α, β-unsaturated carboxylic acid through liquid-phase oxidation of an olefin or an α, β-unsaturated aldehyde.

BACKGROUND ART

As a catalyst for obtaining an α, β-unsaturated carboxylic acid through oxidation of an olefin or an α, β-unsaturated aldehyde in a liquid phase, a noble metal-containing catalyst has been known. For example, methods for producing an α, β-unsaturated carboxylic acid through oxidation of an olefin or an α, β-unsaturated aldehyde in a water-containing solvent in the presence of a silica-supported palladium-containing catalyst are disclosed in examples of Patent Document 1 and Patent Document 2.

Patent Document 1: International Publication No. WO 2005/075,072

Patent Document 2: International Publication No. WO 2005/118,134

DISCLOSURE OF INVENTION

Problem to be Solved by the Invention

However, in the methods disclosed in the examples of Patent Document 1 and Patent Document 2, there was found a problem such that a silica carrier, which is a carrier, dissolved in the water-containing solvent and hence the catalyst activity was lowered during a long time reaction.

Consequently, it is an object of the present invention to provide a method for producing an α, β-unsaturated carboxylic acid from an olefin or an α, β-unsaturated aldehyde, while suppressing dissolution of a silica carrier, which is a carrier for a silica-supported noble metal-containing catalyst, in a water-containing solvent.

Means for Solving the Problem

The present invention is a method for producing an α, β-unsaturated carboxylic acid through oxidation of an olefin or an α, β-unsaturated aldehyde in a water-containing solvent in the presence of a silica-supported noble metal-containing catalyst in a reactor, comprising supplying at least one of silicic acid and ions thereof into the reactor.

EFFECT OF THE INVENTION

According to the present invention, dissolution of a silica carrier, which is a carrier for a silica-supported noble metal-containing catalyst, in a water-containing solvent can be suppressed in the case of producing an α, β-unsaturated carboxylic acid through liquid-phase oxidation of an olefin or an α, β-unsaturated aldehyde.

BEST MODE FOR CARRYING OUT THE INVENTION

The present invention is a method for producing an α, β-unsaturated carboxylic acid through oxidation of an olefin or an α, β-unsaturated aldehyde in a liquid phase. Specifically, the present invention is a method for producing an α, β-unsaturated carboxylic acid through oxidation of an olefin or an α, β-unsaturated aldehyde in a water-containing solvent in the presence of a silica-supported noble metal-containing catalyst in a reactor. Further, when the production is carried out, at least one of silicic acid and ions thereof is supplied into the reactor. In addition, this method can also be applicable to a method for producing an α, β-unsaturated carboxylic acid anhydride through oxidation of an olefin or an α, β-unsaturated aldehyde in a liquid phase.

As the olefin to be supplied to the reactor as a raw material, for example, propylene, isobutylene, and 2-butene can be mentioned. Among them, propylene and isobutylene are preferable. The olefin as a raw material may contain a small amount of a saturated hydrocarbon or a lower saturated aldehyde, or both as impurities. The α, β-unsaturated carboxylic acid to be produced has the same carbon skeleton as the olefin. Specifically, acrylic acid is obtained when the raw material is propylene and methacrylic acid is obtained when the raw material is isobutylene.

As the α, β-unsaturated aldehyde to be supplied to the reactor as a raw material, for example, acrolein, methacrolein, crotonaldehyde, namely, β-methyl acrolein, and cinnamaldehyde, namely, β-phenyl acrolein can be mentioned. Among them, acrolein and methacrolein are preferable. The α, β-unsaturated aldehyde as a raw material may contain a small amount of a saturated hydrocarbon or a lower saturated aldehyde, or both as impurities. The α, β-unsaturated carboxylic acid to be produced is the one in which the aldehyde group in the α, β-unsaturated aldehyde has changed into the carboxyl group. Specifically, acrylic acid is obtained when the raw material is acrolein and methacrylic acid is obtained when the raw material is methacrolein.

Oxidation of the olefin or the α, β-unsaturated aldehyde is carried out in a water-containing solvent. Therefore, a solvent to be supplied to the reactor preferably contains water, however, it may not necessarily contain water when it is supplied because water is formed with the progress of the oxidation reaction. The above-mentioned solvent preferably contains at least one organic solvent selected from the group consisting of t-butanol, cyclohexanol, acetone, methyl ethyl ketone, methyl isobutyl ketone, acetic acid, propionic acid, n-butyric acid, isobutyric acid, n-valeric acid, isovaleric acid, ethyl acetate, and methyl propionate. The amount of the organic solvent when a mixed solvent of water and the organic solvent is supplied is not particularly limited, however, it is preferably 98% by mass or less based on the total mass of the organic solvent and water and more preferably 95% by mass or less, and preferably 30% by mass or more and more preferably 50% by mass or more.

At least one of silicic acid and ions thereof is supplied into the reactor. As the silicic acid, orthosilicic acid and condensates thereof and metasilicic acid and condensates thereof can be mentioned.

In the present invention, the method for supplying at least one of silicic acid and ions thereof into the reactor is not particularly limited, however, it is preferable to prepare a mixture, namely, silicic acid-containing liquid, of at least one of silicic acid and ions thereof with the olefin or the α, β-unsaturated aldehyde, or with the water-containing solvent, and then to supply the silicic acid-containing liquid, the silica-supported noble metal-containing catalyst, and the olefin or the α, β-unsaturated aldehyde to the reactor.

Hereinafter, the case where the silicic acid-containing liquid is prepared and then supplied into the reactor is exemplified.

The silicic acid-containing liquid can be prepared by dissolving silica in the olefin or the α, β-unsaturated aldehyde or in the water-containing solvent. The method for dissolving silica is not particularly limited, however, usually, silica is brought into contact with the olefin or the α, β-unsaturated aldehyde or with the water-containing solvent, and preferably with the water-containing solvent. At least a part of silica contained in the silicic acid-containing liquid thus prepared is dissolved in the olefin or the α, β-unsaturated aldehyde or in the water-containing solvent to be present as at least one of silicic acid and ions thereof. In the silicic acid-containing liquid, undissolved silica may be dispersed as fine particles.

As the method for bringing silica into contact with the olefin or the α, β-unsaturated aldehyde or with the water-containing solvent, any one of a batchwise method, a semi-batchwise method, and a continuous flow method can be adopted. The continuous flow method is preferable from the viewpoint of productivity. As a reactor for such a silica dissolving step, for example, a stirred tank reactor, a packed column reactor, and a bubble column reactor can be mentioned and a continuous flow reactor in which silica is packed in a column is preferably used.

Time for the silica dissolving step is preferably 0.1 hour or more and more preferably 0.2 hour or more, and preferably 8 hours or less and more preferably 6 hours or less. Temperature is preferably 50° C. or above and more preferably 70° C. or above, and preferably 140° C. or below, more preferably 120° C. or below, and furthermore preferably 100° C. or below. As for pressure, either under normal pressure or under pressure can be applied, however, it is preferably 0.5 MPa or lower in gauge pressure and more preferably 0.2 MPa or lower, hereinafter, every pressure is expressed in gauge pressure.

A kind or a production method of silica that is supplied to the reactor in the silica dissolving step is not particularly limited, and for example, silica sol, colloidal silica, silica gel, fumed silica, and white carbon can be mentioned, however, silica gel is preferable. The specific surface area of the silica is not particularly limited, however, it is preferably 50 $m^2/g$ or more and more preferably 100 $m^2/g$ or more, and preferably 1500 $m^2/g$ or less and more preferably 1000 $m^2/g$ or less. The pore volume of the silica is not particularly limited, however, it is preferably 0.1 cc/g or more and more preferably 0.2 cc/g or more, and preferably 2.0 cc/g or less and more preferably 1.5 cc/g or less. In addition, the preferable volume average particle diameter of the silica is not particularly limited, however, it is preferably 0.5 μm or more and more preferably 1.0 μm or more, and preferably 2 mm or less and more preferably 1 mm or less. As for the amount of silica to be used, resistance at the time of passing the solvent through the silica becomes large in the case that the amount of silica is too much and the specific surface area or the strength sharply drops in the case that the amount of silica is too little, so that it is determined taking account of both cases.

The method for measuring silica content in the silicic acid-containing liquid thus prepared is not particularly limited, however, a method in which a pretreatment according to JIS K0101, namely, testing methods for industrial water, article 44.3, total silica, in which sodium carbonate is added and molybdenum-blue absorption spectrophotometry are combined, and a method in which the pretreatment in which sodium carbonate is added and ICP emission spectroscopy are combined can be mentioned. In addition, it is possible to carry out continuous measurement using an apparatus according to JIS K0126, namely, general rules for flow injection analysis. Silica content in a reaction liquid withdrawn from the reactor of the liquid-phase oxidation reaction can also be measured with the same methods mentioned above. The mass of silicon, namely, the amount of silicon, in the silicic acid-containing liquid can be calculated from this silica content.

The silicic acid-containing liquid is usually supplied as it is into the reactor for the liquid-phase oxidation reaction, however, it can also be supplied after its composition is adjusted by water or an organic solvent.

Further, a liquid remaining after operation of separating the catalyst and organic substances such as the α, β-unsaturated carboxylic acid from the reaction liquid withdrawn from the reactor in which the liquid-phase oxidation reaction using the silica-supported noble metal-containing catalyst and the water-containing solvent has been carried out can also be reused as the water-containing solvent containing at least one of silicic acid and ions thereof.

In the case that the reaction type of the liquid-phase oxidation reaction is a continuous reaction, it is preferable to carry out the step of continuously supplying at least one of silicic acid and ions thereof into the reactor and the step of continuously withdrawing at least one of silicic acid and ions thereof from the reactor. The amount of silicon contained in the silicic acid and ions thereof to be supplied into the reactor per 1 hour is preferably 30% or more of the amount of silicon contained in the silicic acid and ions thereof to be withdrawn from the reactor per 1 hour, more preferably 60% or more, and particularly preferably 90% or more, and preferably 130% or less, more preferably 120% or less, and particularly preferably 110% or less. When the above-mentioned ratio is below the fixed range, dissolution of the silica carrier, which is the carrier of the catalyst, in the water-containing solvent is liable to increase. In addition, when the above-mentioned ratio is above the fixed range, deposition of silica in the reactor causing pore blockage of the silica carrier is liable to occur to lower the yield of the α, β-unsaturated carboxylic acid.

The amount of silicon contained in the silicic acid and ions thereof to be supplied into the reactor per 1 hour can be determined from the mass of the silicic acid-containing liquid to be supplied into the reactor per 1 hour and the silica content in the silicic acid-containing liquid. The amount of silicon contained in the silicic acid and ions thereof to be withdrawn from the reactor per 1 hour can be determined from the mass of the reaction liquid to be withdrawn from the reactor per 1 hour and the silica content in the reaction liquid.

The reaction liquid to be withdrawn from the reactor means the reaction liquid remaining after a solid-liquid separation step and after the catalyst has been separated. As a filter to be used in the solid-liquid separation step, a pressure Nutsche filter, board flame filter press, convexo board flame filter press, Emico-Burwell filter press, reversible filter press, Kelly filter, Sweetland filter, Vallez filter, horizontal plate pressure filter, vertical cylindrical pressure leaf filter, continuous cross flow filter, continuous rotary drum pressure filter, continuous double drum pressure filter, continuous drum belt pressure filter, continuous rotary filter press, and continuous pressure leaf filter can be used, however, the cross flow filter is preferably used.

As for the amount of silicon contained in the silicic acid and ions thereof in the silicic acid-containing liquid to be supplied, it is preferably 1 or more based on the equation represented by (the amount of silicon contained in the silicic acid and ions thereof to be supplied into the reactor during the residence time/the mass of the reaction liquid in the reactor)× 1,000,000, more preferably 3 or more, and particularly preferably 5 or more, and preferably 200 or less, more preferably 100 or less, and particularly preferably 50 or less.

In the case that the reaction type of the liquid-phase oxidation reaction is a batchwise reaction, preferable silica content in the silicic acid-containing liquid cannot be absolutely fixed because the composition of the reaction liquid such as concentration of the α, β-unsaturated carboxylic acid or water content changes with the progress of the reaction. The content of silica to be dissolved in the water-containing solvent to be supplied into the reactor is preferably in the range of from 10 to 100% based on the product of (saturated solubility of silica in water at the reaction temperature of the liquid-phase oxidation reaction) and (water content of the water-containing solvent). When the above-mentioned ratio is below the fixed range, dissolution of the silica carrier, which is the carrier of the catalyst, in the water-containing solvent increases. In addition, when the above-mentioned ratio is above the fixed range, there is a case where the reaction at high temperature and high pressure becomes necessary in the silica dissolving step. For example, when 75% by mass aqueous t-butanol solution is supplied as the water-containing solvent at a reaction temperature of 75° C., the silicon content in the water-containing solvent is preferably in the range of from 8.25 ppm to 82.5 ppm as a measured value of silica because the saturated solubility of silica in water at 75° C. is 330 ppm.

The catalyst to be used in the present invention is the one in which a noble metal is supported on a silica carrier. The specific surface area of the silica carrier is preferably 50 $m^2/g$ or more and more preferably 100 $m^2/g$ or more, and preferably 1,500 $m^2/g$ or less and more preferably 1,000 $m^2/g$ or less. As the specific surface area of the silica carrier becomes smaller, production of a catalyst in which its supported components such as palladium are supported more on its surface becomes possible, and as the specific surface area of the silica carrier becomes larger, production of a catalyst in which its supported components are supported more becomes possible. The pore volume of the silica carrier is not particularly limited, however, it is preferably 0.1 cc/g or more and more preferably 0.2 cc/g or more, and preferably 2.0 cc/g or less and more preferably 1.5 cc/g or less.

In addition, the preferable volume average particle diameter of the silica carrier is variable depending on the shape and size of the reactor and is not particularly limited, however, it is preferably 0.5 μm or more and more preferably 1.0 μm or more, and preferably 200 μm or less and more preferably 100 μm or less. As the volume average particle diameter of the carrier becomes larger, separation of the catalyst and the reaction liquid becomes easier, and as the volume average particle diameter of the carrier becomes smaller, the outer surface area of the carrier becomes larger and hence deterioration of the catalyst activity attributed to influence of pore diffusion becomes harder to occur.

The noble metal of the present invention means palladium, platinum, rhodium, ruthenium, iridium, gold, silver, rhenium, or osmium. The noble metal contained in the noble metal-containing catalyst in the present invention may be these metals alone or a mixture of two or more kinds of these metals. Among them, palladium, platinum, rhodium, ruthenium, iridium, or gold is preferable and palladium is particularly preferable.

The noble metal-containing catalyst to be used in the present invention may contain an optional metal besides the noble metal such as bismuth, antimony, or tellurium. When the optional metal besides the noble metal is contained, a method of dissolving a metal compound of the optional metal in the solution of a compound of the noble metal can be used. It is preferable that the amount of the optional metal besides the noble metal in the noble metal-containing catalyst be 50 atomic % or less from the viewpoint of catalyst activity.

A method for loading the noble metal on the carrier is not particularly limited in the preparation of the catalyst, however, it is preferable to load the noble metal on the carrier by means of an impregnation method. In this case, a method of soaking the carrier in a solution of a noble metal salt followed by evaporating the solvent, or what is called a pore filling method in which an amount of a solution of a noble metal salt equivalent to a pore volume of the carrier is absorbed by the carrier and then the solvent is evaporated is particularly preferable.

The noble metal salt to be used is not particularly limited, however, for example, a compound containing a noble metal atom in its oxidation state such as a chloride, oxide, acetate salt, nitrate, sulfate, tetrammine complex salt, or acetylacetonato complex salt of the noble metal is preferable, and among them, a chloride, acetate salt, or nitrate of the noble metal is more preferable. The solvent for dissolving the noble metal salt is not particularly limited as long as it can dissolve the noble metal salt.

In addition, a method in which the noble metal salt is supported on the carrier, then the noble metal salt on the carrier is transformed into a noble metal oxide by heat treatment, and then the oxide is reduced is preferable.

Temperature of the heat treatment is preferably the decomposition temperature of the noble metal salt to be used or higher. Time for the heat treatment is not particularly limited as long as it is enough for transforming the noble metal salt into a noble metal oxide, however, it is preferably 1 hour or more and preferably 12 hours or less.

The reducing agent to be used at the time of reduction of the noble metal oxide is not particularly limited, and for example, hydrazine, formaldehyde, sodium borohydride, hydrogen, formic acid, a formate salt, ethylene, propylene, 1-butene, 2-butene, isobutylene, 1,3-butadien, 1-heptene, 2-heptene, 1-hexene, 2-hexene, cyclohexene, allyl alcohol, methallyl alcohol, acrolein, and methacrolein can be mentioned. Hydrogen, hydrazine, formaldehyde, formic acid, and a formate salt are preferable. These reducing agents can also be used in a combination of two or more kinds.

As a solvent to be used at the time of reduction in a liquid phase, water is preferable, however, solvents like alcohols such as ethanol, 1-propanol, 2-propanol, n-butanol, and t-butanol; ketones such as acetone, methyl ethyl ketone, methyl isobutyl ketone, and cyclohexanone; organic acids such as acetic acid, n-valeric acid, and isovaleric acid; and hydrocarbons such as heptane, hexane, and cyclohexane can be used alone or in a combination of two or more kinds, depending on dispersibility of the carrier. A mixed solvent of these solvents and water can also be used.

When the reducing agent is a gas, it is preferable to carry out reduction in a pressure device such as autoclave to increase solubility of the gas into a solution. In that case, inside the pressure device is pressurized by the reducing agent. The pressure is preferably 0.1 MPa or more and preferably 1.0 MPa or less.

In addition, when the reducing agent is a liquid, a device for carrying out reduction of the noble metal oxide or the noble metal salt is not particularly limited and the reduction can be carried out by adding the reducing agent into a solution of the noble metal oxide or the noble metal salt. In this case, the amount of the reducing agent to be used is not particularly limited, however, it is preferably 1 mole or more and preferably 100 moles or less to 1 mole of the noble metal oxide or the noble metal salt.

The reduction temperature and the reduction time are variable depending on the noble metal oxide, the noble metal salt, or the reducing agent to be used, however, the reduction temperature is preferably −5° C. or above and more preferably 15° C. or above, and preferably 150° C. or below and more preferably 80° C. or below. The reduction time is preferably 0.1 hour or more, more preferably 0.25 hour or more, and furthermore preferably 0.5 hour or more, and preferably 4 hours or less, more preferably 3 hours or less, and furthermore preferably 2 hours or less.

It is preferable to carry out washing of the noble metal-containing catalyst thus obtained with water or an organic solvent. Impurities derived from the noble metal salt such as, for example, a chloride, an acetate group, nitrate group, and sulfate group can be removed by the washing with water or an organic solvent. The method for washing and the number of times of washing are not particularly limited, however, it is preferable to carry out washing to the extent that the impurities can be sufficiently removed because the liquid-phase oxidation of the olefin or the α, β-unsaturated aldehyde is liable to be inhibited depending on the impurities. The catalyst washed may be directly used in the reaction after it is recovered by filtration or centrifugation.

In addition, the recovered catalyst may be dried. The method for drying is not particularly limited, however, it is preferable that the catalyst be dried in air or in an inert gas using a dryer. The dried catalyst can also be activated prior to the use in the reaction, if necessary. The method for activation is not particularly limited, however, for example, a method of heat treatment under a reductive atmosphere in a hydrogen flow can be mentioned. According to this method, an oxidized film on the surface of the noble metal and impurities that have not been removed by washing can be removed.

The noble metal loading ratio of the catalyst to be used in the present invention is not particularly limited, however, it is preferably 0.1% by mass or more based on the carrier before the noble metal is loaded, more preferably 0.5% by mass or more, furthermore preferably 1% by mass or more, and particularly preferably 4% by mass or more. The noble metal loading ratio of the catalyst is preferably 40% by mass or less based on the carrier before the noble metal is loaded, more preferably 30% by mass or less, furthermore preferably 20% by mass or less, and particularly preferably 15% by mass or less.

The reaction for producing an α, β-unsaturated carboxylic acid through oxidation of an olefin or an α, β-unsaturated aldehyde in a water-containing solvent, hereinafter, merely referred to as liquid-phase oxidation reaction, may be either continuous type or batchwise type, however, it is preferably continuous type, from the viewpoint of industrial productivity.

As an oxidant to be used in the liquid-phase oxidation reaction, molecular oxygen is economical and hence preferable. As a source for the molecular oxygen, air is economical and hence preferable, however, pure oxygen or a mixed gas of pure oxygen and air can also be used, and if necessary, a diluted mixed gas in which air or pure oxygen is diluted with nitrogen, carbon dioxide, water vapor, or the like can also be used. The gas such as air is usually supplied in a pressurized state into a reactor such as autoclave.

The concentration of the olefin or the α, β-unsaturated aldehyde which is a raw material is preferably 0.1% by mass or more based on the solvent existing in the reactor, and more preferably 0.5% by mass or more, and preferably 30% by mass or less and more preferably 20% by mass or less.

The amount of the molecular oxygen to be used is preferably 0.1 mole or more based on 1 mole of the olefin or the α, β-unsaturated aldehyde which is a raw material, more preferably 0.2 mole or more, and furthermore preferably 0.3 mole or more, and preferably 20 moles or less, more preferably 15 moles or less, and furthermore preferably 10 moles or less.

The catalyst is usually used in a suspended state in the reaction liquid in which liquid-phase oxidation is carried out, however, it may be used in a fixed bed. The amount of the catalyst to be used is preferably 0.1% by mass or more based on the solution existing in the reactor, more preferably 0.5% by mass or more, and furthermore preferably 1% by mass or more, and preferably 30% by mass or less, more preferably 20% by mass or less, and furthermore preferably 15% by mass or less.

The reaction temperature and the reaction pressure are properly selected depending on the solvent and the raw material of the reaction to be used. The reaction temperature is preferably 30° C. or above and more preferably 50° C. or above. The reaction temperature is preferably 200° C. or below and more preferably 150° C. or below. The reaction pressure is preferably atmospheric pressure, namely, 0 MPa, or above and more preferably 0.5 MPa or above. The reaction pressure is preferably 10 MPa or below and more preferably 5 MPa or below.

EXAMPLES

Hereinafter, the present invention will be more concretely explained by examples and comparative examples, however, the present invention is not limited to these examples. In the following examples and comparative examples, "part" means "part by mass".

(Analysis of an Amount of Silicon in a Silicic Acid-Containing Liquid and in a Reaction Liquid)

The amount of silicon was obtained from the concentration of total silica, namely, silicon dioxide, determined according to "JIS K 0101 44.3, testing methods for industrial water; determination of total silica". Note that, in this method, total silicon atoms contained in silicic acid and ions thereof contained in a silicic acid-containing liquid and in a reaction liquid are presumed as silicon dioxide, namely, silica, and concentration of the silicon dioxide is measured. From this silica content, the amount of silicon is calculated.

Example 1

(Preparation of Catalyst)

To 0.324 part of telluric acid, distilled water having a mass 10 times as much as that of the telluric acid was added to obtain a homogeneous solution. Further, 4.31 parts of palladium nitrate solution, which is equivalent to 1.0 part as palladium, the palladium nitrate solution being 23.2% by mass palladium nitrate-containing nitric acid acidic aqueous solution, manufactured by N.E. CHEMCAT Corporation, was added. Five parts of silica carrier, as a carrier, having a specific surface area of 530 $m^2/g$, a pore volume of 0.68 cc/g, and a median diameter of 52 μm was soaked into the resultant solution and then subjected to evaporation. Subsequently, a thus obtained substance was calcined at 200° C. for 3 hours in air. A catalyst precursor thus obtained was added to 10 parts of 37% by mass aqueous formaldehyde solution, and heated to 70° C. and held at the same temperature for 2 hours while stirred, and filtrated under suction, and then filtrated while washed with 500 parts of warm water to obtain 6.18 parts of a silica-supported catalyst.

(Preparation of a Silicic Acid-Containing Liquid)

To 100 parts of 75% by mass aqueous t-butanol solution which does not contain silicic acid and ions thereof, 1 part of silica having a specific surface area of 530 $m^2/g$, a pore volume of 0.68 cc/g, and a median diameter of 52 μm was added and heated at 75° C. for 40 hours, and then filtrated to obtain a 75% by mass aqueous t-butanol solution in which 15.8 ppm of silica is dissolved, namely, silicic acid-containing liquid. The amount of silicon contained in silicic acid and ions thereof contained in 75 parts of the silicic acid-containing liquid was $5.53 \times 10^{-4}$ part.

(Evaluation of Reaction)

To an autoclave, total amount of the catalyst obtained by the aforementioned method, which is equivalent to 1.0 part as palladium, and 75.0 parts of the above-mentioned silicic acid-containing liquid were introduced, and the autoclave was shut tight. Subsequently, 1.96 parts of isobutylene which does not contain silicic acid and ions thereof was introduced and stirring of the resultant mixture was started at a number of revolution of 1,000 rpm, and the temperature of the mixture was raised to 75° C. After the raising of the temperature was completed, nitrogen was introduced into the autoclave to the internal pressure of 2.4 MPa and then compressed air was introduced into the autoclave to the internal pressure of 4.8 MPa. Each time when the internal pressure dropped by 0.1 MPa, the internal pressure being 4.7 MPa, oxygen was introduced into the autoclave by 0.1 MPa, and this operation was repeated during the reaction. At the reaction time of 45 minutes, the autoclave was opened to the atmosphere and the reaction was finished. The reaction liquid containing the catalyst was withdrawn from the autoclave and the catalyst was separated with a membrane filter having 0.5 μaperture to recover 76.0 parts of the reaction liquid.

The reaction liquid thus recovered was analyzed with gas chromatography, and the number of moles of methacrylic acid produced was quantitatively determined. The yield of methacrylic acid was calculated from the number of moles of isobutylene supplied and the number of moles of methacrylic acid produced. The yield of methacrylic acid anhydride was obtained in the same manner.

In addition, the content of silica dissolving in the recovered reaction liquid was 17.0 ppm, and the amount of silicon contained in silicic acid and ions thereof contained in the reaction liquid was $6.03 \times 10^{-4}$ part. The change in the amount of silicon before and after the reaction was small, so that the amount silica carrier, as a carrier, dissolved in 75% by mass aqueous t-butanol solution as a water-containing solvent was small. The results are shown in Table 1.

Comparative Example 1

(Preparation of Catalyst)

The same procedure as in Example 1 was carried out to prepare the catalyst.

(Evaluation of Reaction)

The same procedure as in Example 1 was carried out except that 75% by mass aqueous t-butanol solution which does not contain silicic acid and ions thereof thereof was used instead of the silicic acid-containing liquid. The content of silica dissolving in 76.0 parts of the recovered reaction liquid was 16.8 ppm, and the amount of silicon contained in silicic acid and ions thereof contained in the reaction liquid was $5.96 \times 10^{-4}$ part. The change in the amount of silicon before and after the reaction was large, so that the amount silica carrier, as a carrier, dissolved in 75% by mass aqueous t-butanol solution as a water-containing solvent was larger than that in Example 1. The results are shown in Table 1.

TABLE 1

| | Amount of silicon in the reaction liquid before the reaction (A) | Amount of silicon in the reaction liquid after the reaction (B) | Change in the amount of silicon (B) − (A) | Yield of methacrylic acid | Yield of methacrylic acid anhydride |
|---|---|---|---|---|---|
| Example 1 | $5.53 \times 10^{-4}$ part | $6.03 \times 10^{-4}$ part | $0.50 \times 10^{-4}$ part | 34.2% | 17.5% |
| Comp. Ex. 1 | Not detected | $5.96 \times 10^{-4}$ part | $5.96 \times 10^{-4}$ part | 33.2% | 12.9% |

Example 2

(Preparation of Catalyst)

To 5.395 parts of telluric acid, which is equivalent to 3 parts as tellurium, distilled water having a mass 20 times as much as that of the telluric acid was added to obtain a homogeneous solution. Further, 107.8 parts of palladium nitrate solution, which is equivalent to 25 parts as palladium, the palladium nitrate solution being 23.2% by mass palladium nitrate-containing nitric acid acidic aqueous solution, manufactured by N.E. CHEMCAT Corporation, was added. One hundred and twenty-five parts of silica carrier, as a carrier, having a specific surface area of 530 m$^2$/g, a pore volume of 0.68 cc/g, and a median diameter of 52 μm were soaked into the resultant solution and then subjected to evaporation. Subsequently, a thus obtained substance was calcined at 200° C. for 3 hours in air. A catalyst precursor thus obtained was added to 250 parts of 37% by mass aqueous formaldehyde solution, and heated to 70° C. and held at the same temperature for 2 hours while stirred, and filtrated under suction, and then filtrated while washed with 10,000 parts of warm water to obtain 153 parts of a silica-supported catalyst.

(Continuous Preparation of a Silicic Acid-Containing Liquid)

As a silica dissolving step, 125 parts of silica having a specific surface area of 530 m$^2$/g, a pore volume of 0.68 cc/g, and a median diameter of 52 μm and 1,800 parts of 75% by mass aqueous t-butanol solution were introduced into a stainless steel stirred tank reactor with a jacket, and pressurized to 6.0 MPa with nitrogen gas, and the temperature of the liquid phase was adjusted to 110° C. To this reactor, 3,510 parts per 1 hour of the 75% by mass aqueous t-butanol solution containing 200 ppm of p-methoxyphenol as a polymerization inhibitor were continuously supplied. And 3,510 parts per 1 hour of the solvent was continuously withdrawn from the reactor so that the residence time could be adjusted to 0.5 hour and the reaction liquid surface could be kept at the same level. The content of silica dissolving in the withdrawn silicic acid-containing liquid was 21.2 ppm, and the amount of silicon in this liquid per 1 hour was $3.47 \times 10^{-2}$ part.

(Evaluation of Reaction)

To a stainless steel stirred tank reactor with a jacket which is different from the one used for supplying the solvent, 153 parts of the silica-supported catalyst and 1,900 parts of 75% by mass aqueous t-butanol solution were introduced, and the gas phase of the reactor was pressurized to 4.8 MPa with nitrogen gas, and the temperature of the liquid phase was adjusted to 110° C. To the reactor, 3510 parts per 1 hour of the above-mentioned silicic acid-containing liquid and 843 parts per 1 hour of isobutylene were continuously supplied. And the reaction liquid was continuously withdrawn from the reactor so that the residence time could be adjusted to 0.5 hour and the reaction liquid surface could be kept at a certain level.

Subsequently, pressurized air, oxygen concentration being 21% by volume, was continuously supplied to the liquid phase of the reactor through a sparger made of sintered metal while supply of the nitrogen gas was continued to keep the pressure of the gas phase constant, and the liquid-phase oxidation reaction was started. The amount of supply of the pressurized air was controlled such that the concentration of oxygen in the state of unreacted oxygen diluted with nitrogen gas was kept at about 6% by volume. The reaction liquid and the exhaust gas were properly sampled and analyses of the raw materials and the products were carried out using gas chromatograph, manufactured by Shimadzu Corporation, equipped with a FID or TCD detector. It was confirmed that the reaction liquid composition and the exhaust gas composition became almost stationary after a lapse of 4 hours from the start of the reaction.

Accordingly, sampling and analyses of the reaction liquid and the exhaust gas were carried out, and it was found that the amount of the reaction liquid was 3,840 parts per 1 hour, the content of silica dissolving in the reaction liquid was 20.4 ppm, and the amount of silicon contained in silicic acid and ions thereof contained in the reaction liquid was $3.66 \times 10^{-2}$ part. The change in the amount of silicon between the silicic acid-containing liquid supplied and the reaction liquid withdrawn was small, so that the amount silica carrier, as a carrier, dissolved in the water-containing solvent was small. The results are shown in Table 2. In addition, 162 parts per 1 hour of methacrylic acid and 46 parts per 1 hour of methacrylic acid anhydride were produced. The results are shown in Table 3.

Comparative Example 2

(Preparation of Catalyst)

The same procedure as in Example 2 was carried out to prepare the catalyst.

(Water-Containing Solvent)

The same procedure as in Example 2 was carried out except that silica was not introduced into the reactor in the silica dissolving step, and 3,800 parts per 1 hour of the water-containing solvent was continuously withdrawn from the reactor. Silica was not detected from the water-containing solvent withdrawn.

(Evaluation of Reaction)

The same procedure as in Example 2 was carried out except that 3,800 parts per 1 hour of the above-mentioned water-containing solvent which did not contain silicic acid and ions thereof and 938 parts per 1 hour of isobutylene were continuously supplied. The amount of the reaction liquid after a lapse of 4 hours from the start of the reaction was 4,240 parts per 1 hour. The content of silica dissolving in the reaction liquid was 19.5 ppm, and the amount of silicon contained in silicic acid and ions thereof contained in the reaction liquid was $3.86 \times 10^{-2}$ part. The change in the amount of silicon between the water-containing solvent supplied and the reaction liquid withdrawn was large, so that the amount of silica carrier, which is a carrier, dissolved in the water-containing solvent was larger than that in Example 2. The results are shown in Table 2. In addition, 115 parts per 1 hour of methacrylic acid and 39 parts per 1 hour of methacrylic acid anhydride were produced. The results are shown in Table 3.

TABLE 2

|  | Amount of silicon in the liquid supplied (A) | Amount of silicon in the reaction liquid withdrawn (B) | Change in the amount of silicon (B) − (A) |
|---|---|---|---|
| Example 2 | $3.47 \times 10^{-2}$ part/H | $3.66 \times 10^{-2}$ part/H | $0.19 \times 10^{-2}$ part/H |
| Comp. Ex. 2 | Not detected | $3.86 \times 10^{-2}$ part/H | $3.86 \times 10^{-2}$ part/H |

TABLE 3

|  | Amount of the reaction liquid | Amount of isobutylene supplied | Methacrylic acid produced | Methacrylic acid anhydride produced |
|---|---|---|---|---|
| Example 2 | 3,840 parts/H | 843 parts/H | 162 parts/h | 46 parts/h |
| Comp. Ex. 2 | 4,240 parts/H | 938 parts/H | 115 parts/H | 39 parts/H |

As described so far, when an α, β-unsaturated carboxylic acid is produced through liquid-phase oxidation of an olefin or an α, β-unsaturated aldehyde, dissolution of a silica carrier, which is a carrier for a silica-supported noble metal-containing catalyst, in a water-containing solvent could be suppressed.

What is claimed is:

1. A method for producing an α, β-unsaturated carboxylic acid comprising oxidizing an olefin or an α, β-unsaturated aldehyde in a solvent comprising water in the presence of a silica-supported noble metal catalyst in a reactor, comprising supplying at least one of silicic acid and ions thereof into the reactor and continuously withdrawing at least one of silicic acid and ions thereof from the reactor, wherein an amount of silicon present in the silicic acid and ions thereof to be supplied into the reactor per 1 hour is 30 to 130% of an amount of silicon present in the silicic acid and ions thereof to be withdrawn from the reactor per 1 hour.

2. The method for producing an α, β-unsaturated carboxylic acid according to claim 1, wherein the method comprises preparing a liquid comprising silicic acid, in which at least one of the silicic acid and ions thereof is present in the olefin or the α, β-unsaturated aldehyde or in the solvent comprising water, and oxidizing the olefin or the α, β-unsaturated aldehyde by supplying the silica-supported noble metal catalyst, the olefin or the α, β-unsaturated aldehyde, and the liquid comprising silicic acid, into the reactor.

3. The method for producing an α, β-unsaturated carboxylic acid according to claim 2, wherein, in the preparing the liquid comprising silicic acid, the liquid comprising silicic acid is prepared by bringing silica into contact with the olefin or the α, β-unsaturated aldehyde or with the solvent comprising water.

4. The method for producing an α, β-unsaturated carboxylic acid according to claim 1, wherein the method comprises preparing a liquid comprising silicic acid, in which at least one of the silicic acid and ions thereof is present in the olefin or the α, β-unsaturated aldehyde or in the solvent comprising water, and oxidizing the olefin or the α, β-unsaturated aldehyde by supplying the silica-supported noble metal catalyst, the olefin or the α, β-unsaturated aldehyde, and the liquid comprising silicic acid into the reactor.

5. The method for producing an α, β-unsaturated carboxylic acid according to claim 4, wherein, in the preparing the liquid comprising silicic acid, the liquid comprising silicic acid is prepared by bringing silica into contact with the olefin or the α, β-unsaturated aldehyde or with the solvent comprising water.

6. The method for producing an α, β-unsaturated carboxylic acid according to claim 1, wherein the olefin is selected from the group consisting of propylene, isobutylene, and 2-butene.

7. The method for producing an α, β-unsaturated carboxylic acid according to claim 1, wherein the α, β-unsaturated aldehyde is selected from the group consisting of acrolein, methacrolein, crotonaldehyde, and cinnamaldehyde.

8. The method for producing an α, β-unsaturated carboxylic acid according to claim 1, wherein the solvent comprising water further comprises at least one organic solvent selected from the group consisting of t-butanol, cyclohexanol, acetone, methyl ethyl ketone, methyl isobutyl ketone, acetic acid, propionic acid, n-butyric acid, isobutyric acid, n-valeric acid, isovaleric acid, ethyl acetate, and methyl propionate.

9. The method for producing an α, β-unsaturated carboxylic acid according to claim 1, wherein the silicic acid is orthosilicic acid and condensates thereof or metasilicic acid and condensates thereof.

10. The method for producing an α, β-unsaturated carboxylic acid according to claim 1, wherein the liquid comprising silicic acid is prepared by a process comprising dissolving silica in the olefin or the α, β-unsaturated aldehyde or in the solvent comprising water.

11. The method for producing an α, β-unsaturated carboxylic acid according to claim 1, wherein the liquid comprising silicic acid further comprises undissolved silica dispersed as fine particles.

12. The method for producing an α, β-unsaturated carboxylic acid according to claim 10, wherein the silica is selected from the group consisting of silica sol, colloidal silica, silica gel, fumed silica, and white carbon.

13. The method for producing an α, β-unsaturated carboxylic acid according to claim 10, wherein the silica has a specific surface area of from 50 m$^2$/g to 1500 m$^2$/g.

14. The method for producing an α, β-unsaturated carboxylic acid according to claim 10, wherein the silica has a pore volume of from 0.1 cc/g to 2.0 cc/g.

15. The method for producing an α, β-unsaturated carboxylic acid according to claim 10, wherein the silica has volume average particle diameter of from 0.5 μto 2 mm.

16. The method for producing an α, β-unsaturated carboxylic acid according to claim 1, wherein the amount of silicon contained in the silicic acid and/or ions thereof in the liquid comprising silicic acid is 1 or more based on the equation represented by (the amount of silicon contained in the silicic acid and/or ions thereof to be supplied into the reactor during the residence time/the mass of the reaction liquid in the reactor)×1,000,000.

17. The method for producing an α, β-unsaturated carboxylic acid according to claim 1, wherein a noble metal is supported on a silica carrier, and the specific surface area of the silica carrier is from 50 m$^2$/g to 1,500 m$^2$/g.

18. The method for producing an α, β-unsaturated carboxylic acid according to claim 17, wherein the pore volume of the silica carrier is from 0.1 cc/g to 2.0 cc/g.

19. The method for producing an α, β-unsaturated carboxylic acid according to claim 17, wherein the volume average particle diameter of the silica carrier is from 0.5 μm to 200 μm.

* * * * *

UNITED STATES PATENT AND TRADEMARK OFFICE
CERTIFICATE OF CORRECTION

PATENT NO. : 8,058,473 B2  
APPLICATION NO. : 12/521670  
DATED : November 15, 2011  
INVENTOR(S) : Toshiki Matsui et al.

It is certified that error appears in the above-identified patent and that said Letters Patent is hereby corrected as shown below:

On the title page, Item (54), and in column 1, the title is incorrect. Item (54) and column 1, should read:

-- METHOD FOR PRODUCING ALPHA, BETA-UNSATURATED CARBOXYLIC ACID --.

Signed and Sealed this
Fifteenth Day of May, 2012

David J. Kappos
*Director of the United States Patent and Trademark Office*